US009002465B2

(12) United States Patent
Ranu

(10) Patent No.: US 9,002,465 B2
(45) Date of Patent: Apr. 7, 2015

(54) VERIFYING CORRECT OPERATION OF AN IMPLANTABLE NEUROSTIMULATOR DEVICE USING CURRENT DISTRIBUTION CIRCUITRY

(71) Applicant: Boston Scientific Neuromodulation Corporation, Valencia, CA (US)

(72) Inventor: Emarit Ranu, Fort Collins, CO (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

(21) Appl. No.: 13/776,211

(22) Filed: Feb. 25, 2013

(65) Prior Publication Data

US 2013/0268025 A1 Oct. 10, 2013

Related U.S. Application Data

(60) Provisional application No. 61/621,264, filed on Apr. 6, 2012.

(51) Int. Cl.
*A61N 1/08* (2006.01)
*G01R 31/00* (2006.01)
*A61N 1/36* (2006.01)
*A61N 1/39* (2006.01)

(52) U.S. Cl.
CPC ............ *G01R 31/00* (2013.01); *A61N 1/36128* (2013.01); *A61N 1/3931* (2013.01); *A61N 1/08* (2013.01); *A61N 1/36142* (2013.01)

(58) Field of Classification Search
CPC .................................................. A61N 1/3931
See application file for complete search history.

(56) References Cited

U.S. PATENT DOCUMENTS

| 6,101,410 | A | 8/2000 | Panescu et al. |
| 6,516,227 | B1 | 2/2003 | Meadows et al. |
| 7,444,181 | B2 | 10/2008 | Shi et al. |
| 7,539,538 | B2 | 5/2009 | Parramon et al. |
| 7,684,869 | B2 | 3/2010 | Bradley et al. |
| 8,467,872 | B2 * | 6/2013 | Hareland .................. 607/27 |
| 2007/0038250 | A1 | 2/2007 | He et al. |
| 2007/0100399 | A1 | 5/2007 | Parramon et al. |
| 2010/0106219 | A1 | 4/2010 | Torgerson |
| 2011/0307032 | A1 | 12/2011 | Goetz et al. |
| 2013/0006315 | A1 | 1/2013 | Lee |

FOREIGN PATENT DOCUMENTS

| WO | 2007075974 A2 | 7/2007 |
| WO | 2010051317 A1 | 5/2010 |

OTHER PUBLICATIONS

International Search Report and Written Opinion regarding application No. PCT/US2013/027746 dated Jun. 27, 2013.

* cited by examiner

Primary Examiner — Michael Kahelin
(74) Attorney, Agent, or Firm — Lewis & Reese, PLLC

(57) ABSTRACT

Monitoring circuitry for an implantable stimulator device is disclosed. A switching matrix allows current from a current source to be distributed to any of a plurality of electrodes. A voltage drop across the active switches in the switch matrix is monitored and is compared to an expected voltage based upon the amplitude of the current and the known on resistance of the switch. If the monitored and expected voltages differ significantly, then a failure condition can be inferred, and an appropriate action can be taken, such shutting down stimulation. Using the already-existing switches in the switching matrix in this fashion is beneficial because it allows the current through the electrodes to be monitored without providing additional structures in the therapeutic current path, which would increase complexity and add unwanted resistance.

42 Claims, 17 Drawing Sheets

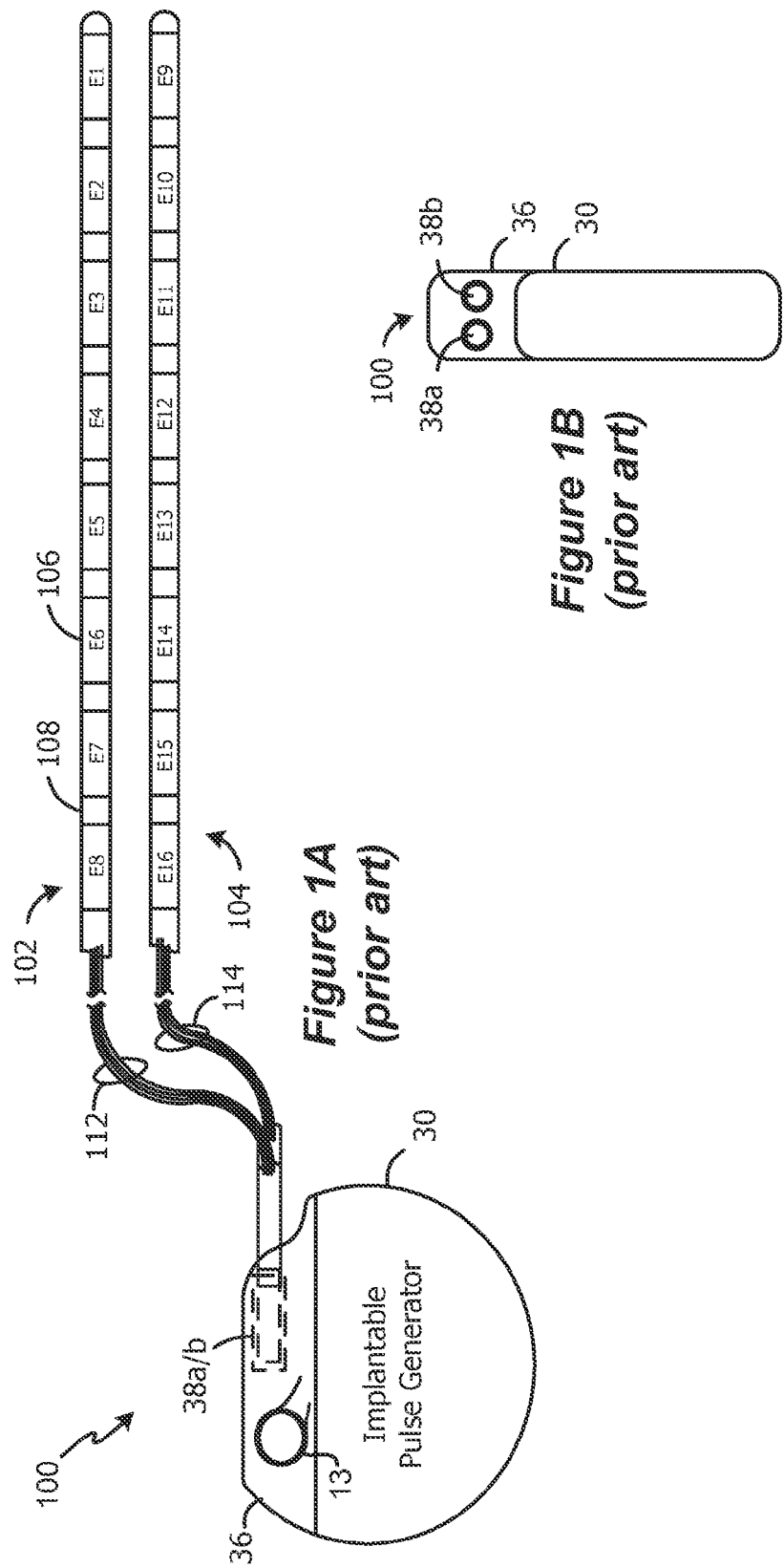

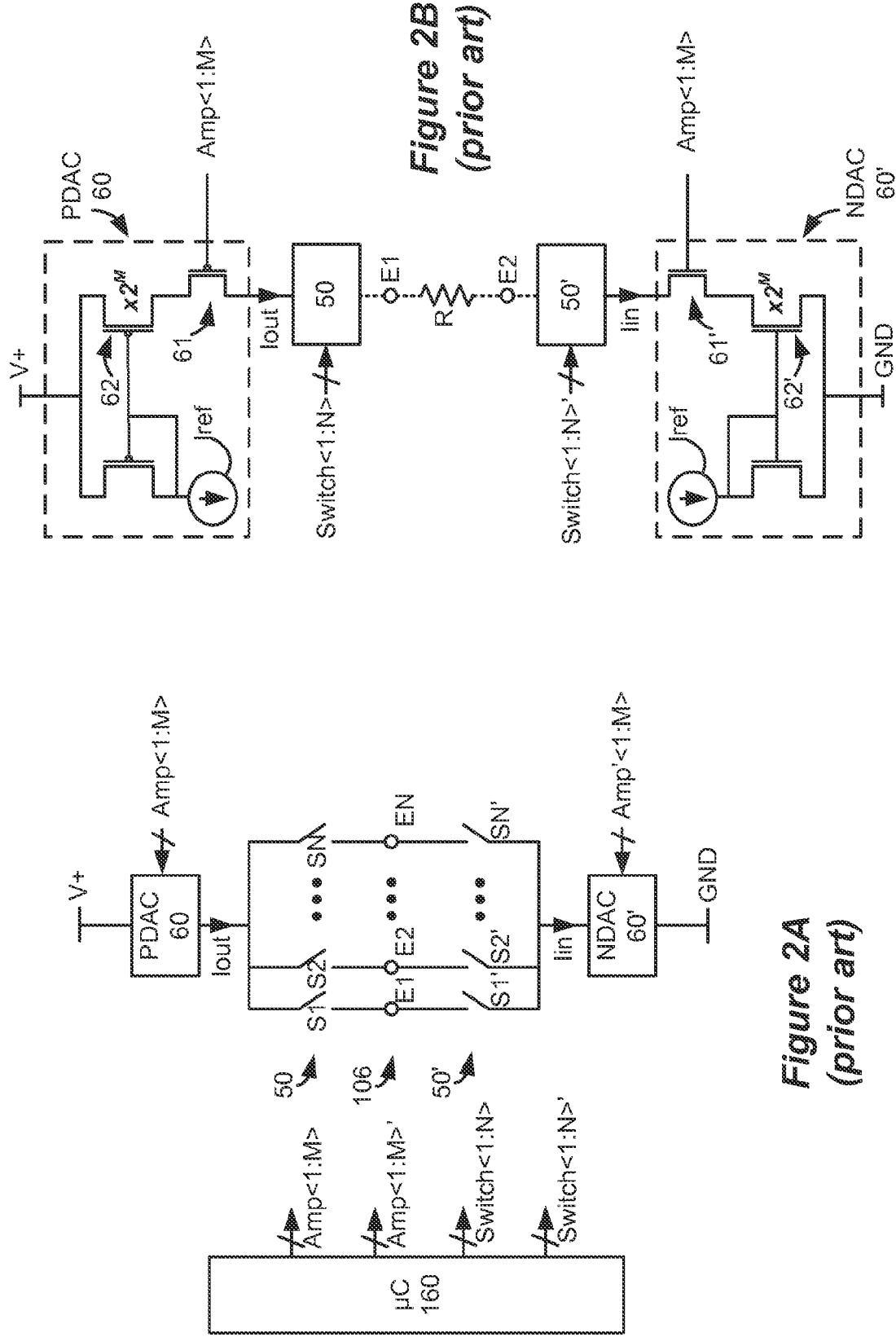

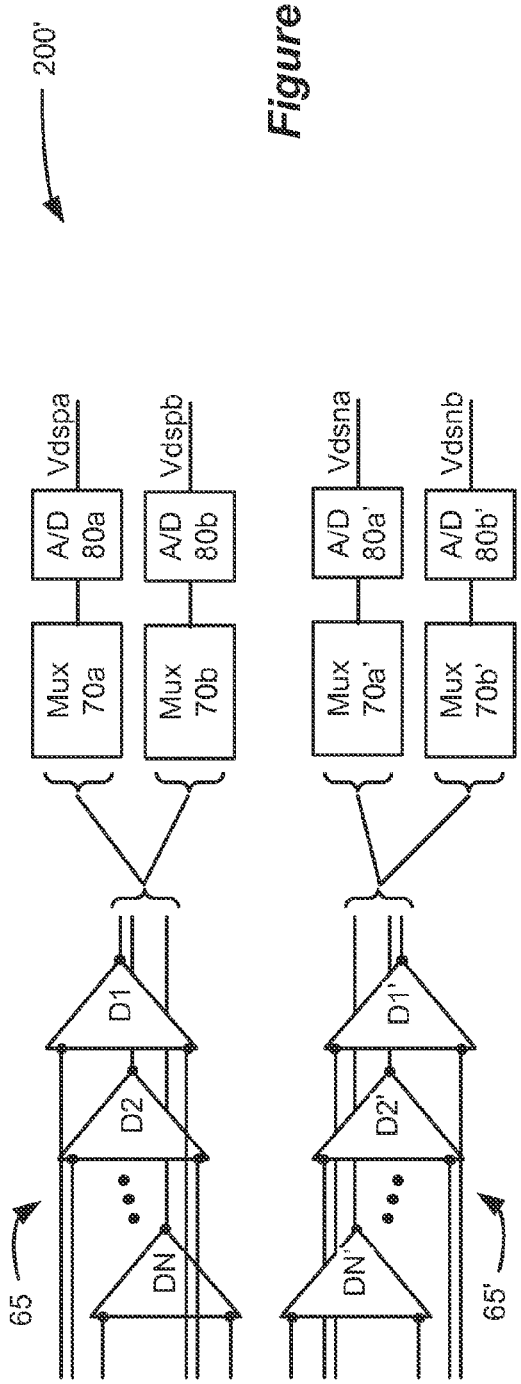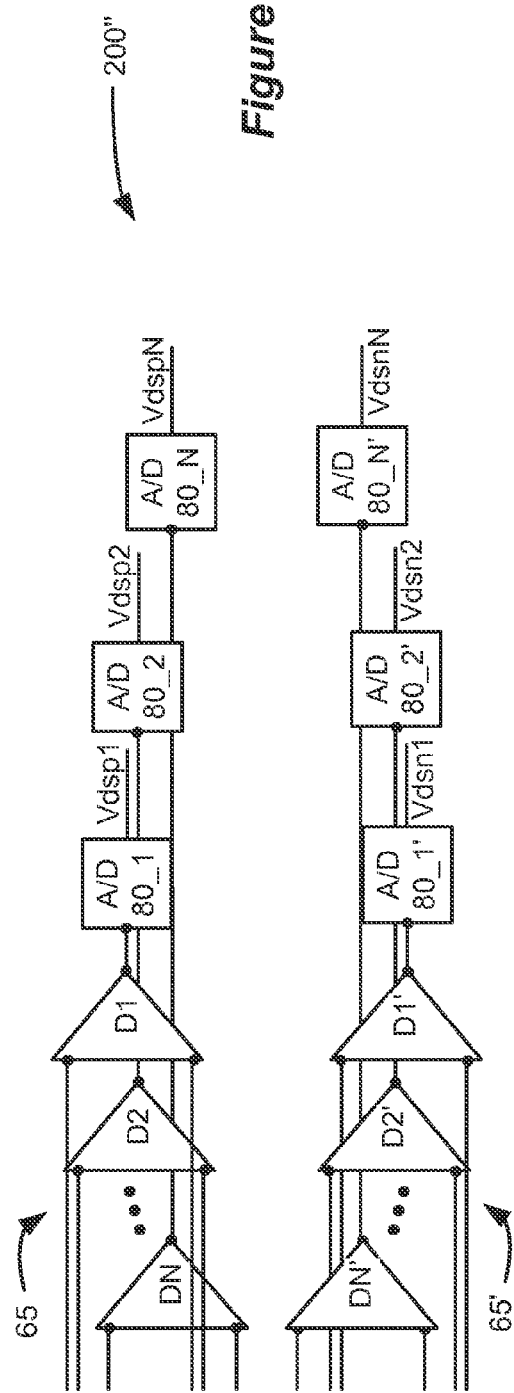

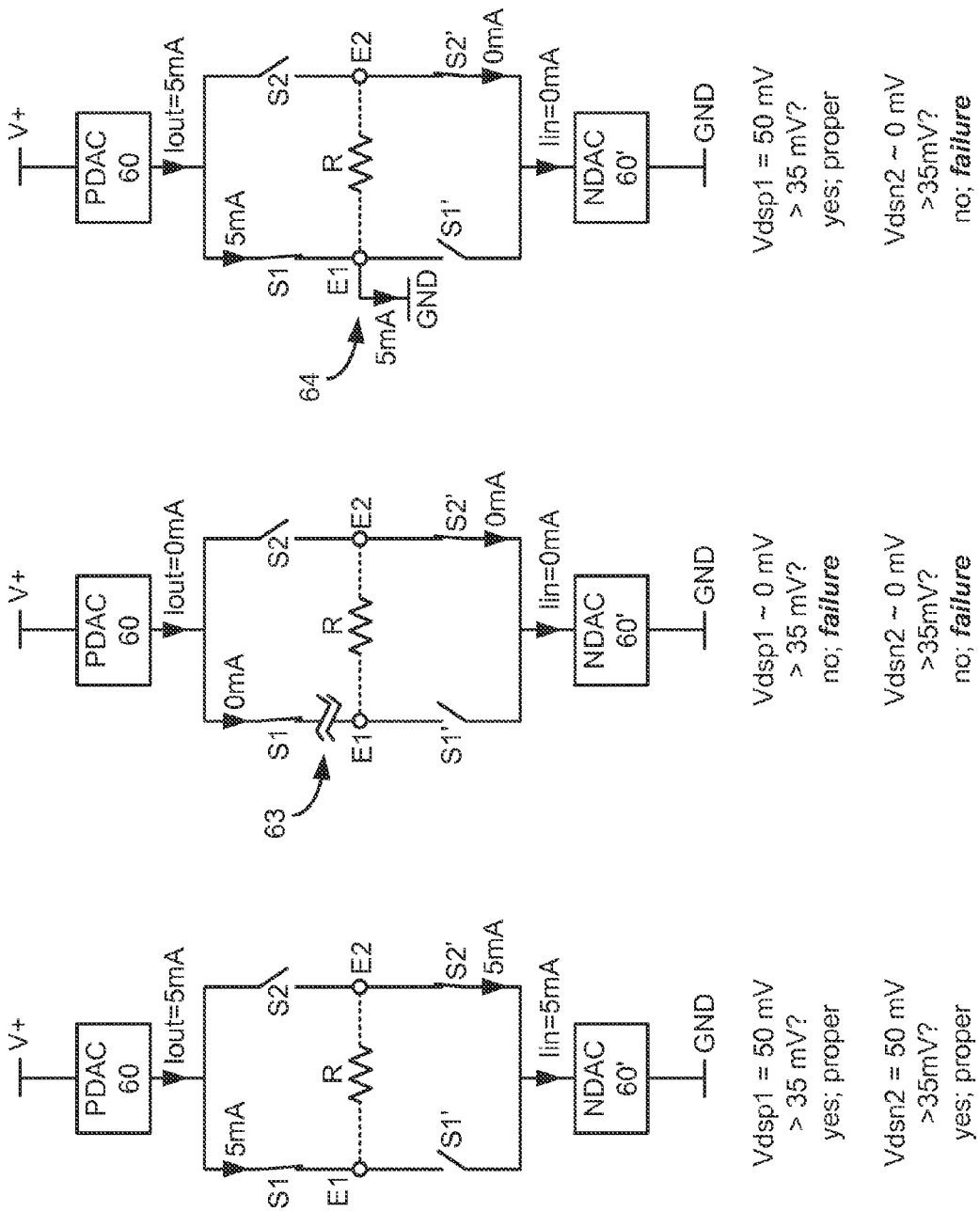

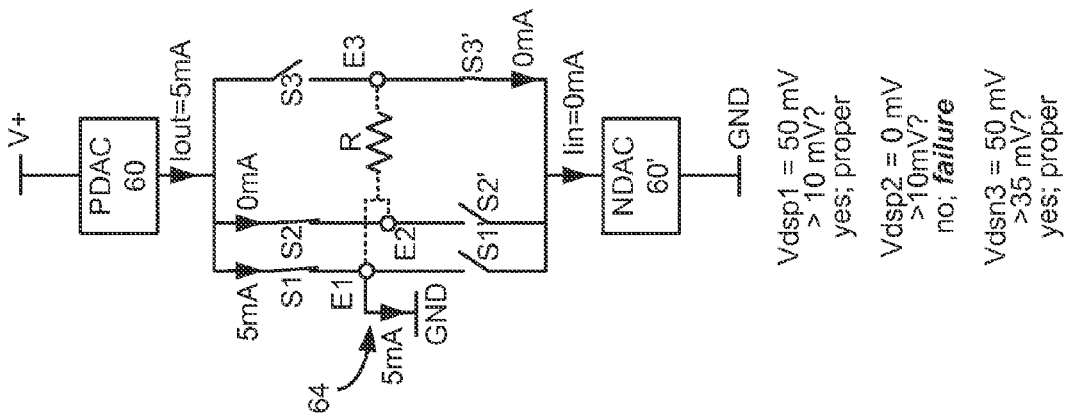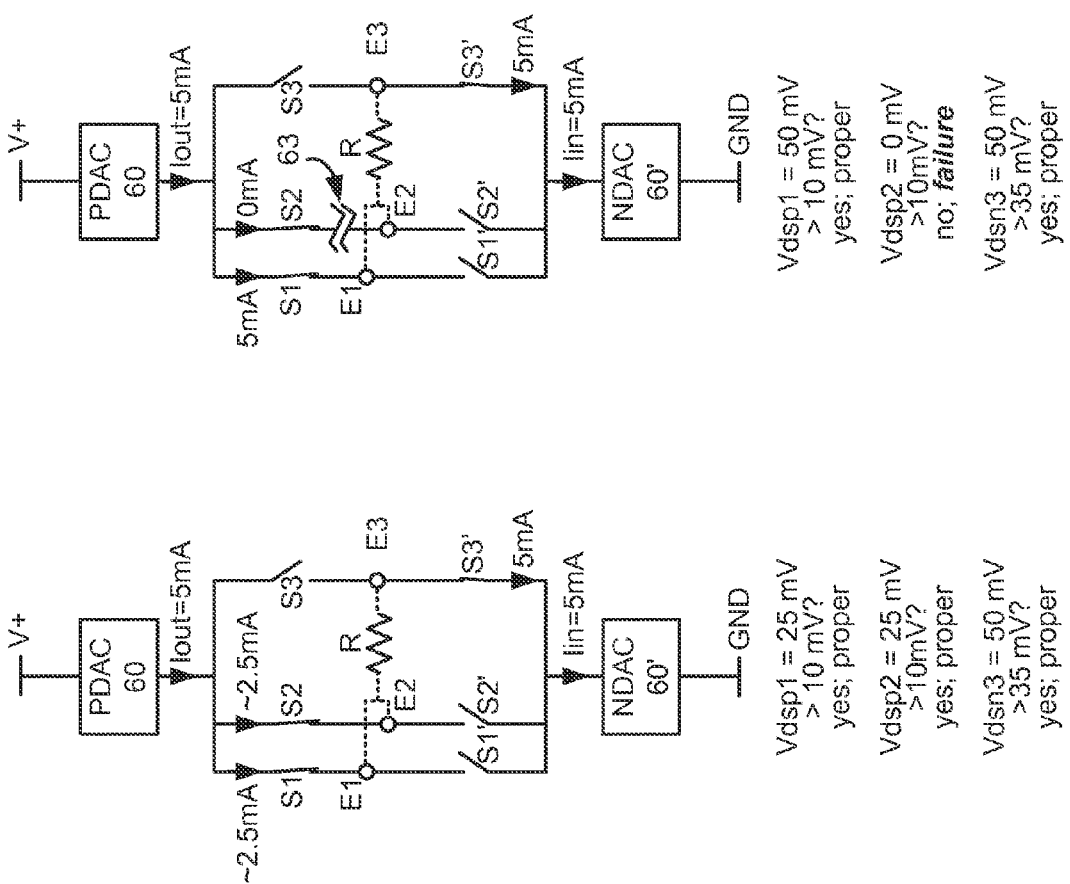

VERIFYING CORRECT OPERATION OF AN IMPLANTABLE NEUROSTIMULATOR DEVICE USING CURRENT DISTRIBUTION CIRCUITRY

CROSS REFERENCE TO RELATED APPLICATIONS

This is a non-provisional filing of U.S. Provisional Application Ser. No. 61/621,264, filed Apr. 6, 2012, which is incorporated herein by reference and to which priority is claimed.

FIELD OF THE INVENTION

The present invention relates generally to implantable neurostimulator devices, and more particularly to monitoring correct operation of the neurostimulator using switches used to route current between the electrodes.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, etc. The description that follows will generally focus on the use of the invention within a Spinal Cord Stimulation (SCS) system, such as that disclosed in U.S. Pat. No. 6,516,227. However, the present invention may find applicability in any implantable stimulator.

As shown in FIGS. 1A and 1B, a SCS system typically includes an Implantable Pulse Generator (IPG) 100, which includes a biocompatible device case 30 formed of a conductive material such as titanium for example, or formed of a non-conductive ceramic. The case 30 typically holds the circuitry and battery 26 necessary for the IPG to function, although IPGs can also be powered via external RF energy and without a battery. The IPG 100 includes one or more electrode arrays (two such arrays 102 and 104 are shown), each containing several electrodes 106. The electrodes 106 are carried on a flexible body 108, which also houses the individual electrode leads 112 and 114 coupled to each electrode. In the illustrated embodiment, there are eight electrodes on array 102, labeled E1-E8, and eight electrodes on array 104, labeled E9-E16, although the number of arrays and electrodes is application specific and therefore can vary. The arrays 102, 104 couple to the IPG 100 using lead connectors 38*a* and 38*b*, which are fixed in a non-conductive header material 36, which can comprise epoxy for example.

FIGS. 2A and 2B show circuitry within the IPG 100 for distributing a therapeutic current, Iout=Iin, between the various electrodes. This current is usually provided as pulses. Shown are a single constant current source 60 and a single constant current sink 60'. Because the current source 60 is formed from P-channel transistors, and because its analog output current, Iout, is set by digital signals (Amp<1:M>), the current source 60 is referred to as a P Digital-to-Analog converter, or "PDAC" 60. Similarly, because the current sink 60' is formed from N-channel transistors, and because its analog input current, Iin, is set by digital signals (Amp<1:M>'), the current sink 60 is referred to as a N Digital-to-Analog converter, or "NDAC" 60'. (Note that prime symbols are used in conjunction with the sink circuitry).

As just mentioned, the current output from, or input to, the PDAC 60 and NDAC 60' are set by digital amplitude signals Amp and Amp' respectively. There may be M of such digital signals, which ultimately issue from some type of control circuitry 160 in the IPG 100, such as a microcontroller. It is typical that the PDAC 60 and NDAC 60' are programmed by Amp and Amp' to source and sink the same current magnitude, i.e., Iout=Iin. In this way, current injected into the patient's tissue, R (FIG. 2B), from one electrode is drawn back into the IPG 100, and thus surplus charge will not accumulate in the patient.

As is well known, and discussed further in U.S. Patent Application Publication 2007/0038250, which is incorporated herein by reference in its entirety, PDAC 60 and NDAC 60' comprise current mirrors which amplify a reference current, Iref, to produce the desired source and sunk currents, Iout and Iin, in accordance with the digital signals Amp and Amp'. Each signal Amp<x> and Amp<x>' controls a switch 61 to cause $2^{x-1}$ current mirror transistors 62 and 62' to be placed in parallel to contribute to the current. This allows the produced currents, Iout and Iin, to be produced as a scalar k of the reference current, i.e., Iout=Iin=kIref. For example, to produce an output current, Iout, of 11Iref, Amp can be set to <00001011>, which places 1+2+8=11 current mirror transistors 62 in parallel. However, this means of digitally setting the output and input currents is merely one example, and other means of setting these currents can also be used, such as are disclosed in the '250 Publication. Ultimately, current flows through the PDAC 60, the tissue R, and the NDAC 60' by virtue of a compliance voltage (V+) coupled to the PDAC 60, and a reference potential (ground; GND) coupled to the NDAC 60'.

Switch matrices 50 and 50' allow the current sourced and sunk by PDAC 60 and NDAC 60' to be distributed to any of the electrodes E1-EN. For example, in FIG. 2B, electrode E1 has been selected to receive the sourced current Iout, while electrode E2 has been selected to receive the sunk current, Iin, thus allowing current to flow through the tissue R between these two electrodes. Selection of the electrodes occurs at switching matrices 50 and 50', and in this example, there are N switches S1-SN and S1'-SN' in each matrix 50 and 50' to allow distribution of the currents to each of the N electrodes, E1-EN. Selection of the switches occurs in accordance with switching control signals Switch<1:N> and Switch'<1:N>, which again can be issued by the control circuitry 160. Thus, to select electrodes E1 and E2 as shown in FIG. 2B, switch S1 has been turned on by switch control signal Switch<1>, while switch S2' has been turned on by switch control signal Switch<2>'. Which of the electrodes are chosen, as well of the amplitude, frequency and duration of the pulses occurring at those electrodes, will be dictated by the patient or clinician, usually based on experimentation as to which settings are most effective, for example, to alleviate the patient's pain or other symptoms.

The inventor has noticed that the current distribution architecture of FIG. 2A and 2B may not function properly if the IPG 100 experiences certain types of failures. FIG. 3A illustrates the IPG 100 functioning properly, passing 5 mA out electrode E1, through the tissue R, and back into electrode E2. FIGS. 3B and 3C show various failures that affect this desired current flow. In FIG. 3B, there is an open circuit 63 in the path going to electrode E1. This failure could occur anywhere along the path from the PDAC 60 to the electrode E1, including inside the case 30, in the internal connections between the IPG 100 and the lead connectors 38*a* and 38*b*, in the lead connectors 38a and 38b, in the leads 112 or 114 themselves, or where the leads 112 or 114 connect to the ring electrodes 106 on the arrays 102 or 104. For example, the lead 112 leading to electrode E1 could have been damaged when it was implanted in the patient, or that lead might be making a poor connection to the contact in its lead connector 38a or 38b. When this failure condition occurs, no current will flow through switch S1 by virtue of the open circuit 63. Likewise, because electrode E2 is isolated from the compliance voltage V+ ultimately used to drive the current, the current through S2' will also equal zero. Thus, no current flows, despite the programming of the PDAC 60 and NDAC 60'.

In FIG. 3C, there is a short circuit 64 between electrode E1 and ground (GND). This failure can again occur anywhere along the path from the PDAC 60 to the electrode E1. Assuming the short 64 is of significantly lower resistance than the tissue R, the majority of current output from the PDAC 60 (5 mA) will flow though the short 64 to ground. As a result, no current (or negligible current) would flow through the tissue R, and E2 is effectively coupled to ground via the short 64. Because the NDAC 60' is referenced to ground, no potential exists to drive a current at electrode E2, and thus no current (or negligible current) will flow through switch S2'.

FIGS. 4A-4C are analogous to FIGS. 3A-3C, but show more-complicated examples in which two electrodes (E1 and E2) are chosen to receive the sourced current, Iout=5 mA, while electrode E3 receives the entirety of this current, Iin=5 mA. Splitting either the sourced or sunk current between two or more electrodes can be therapeutically useful for a particular patient. Alternatively, it can be useful to at least temporarily split the sourced or sunk current in this fashion while experimentally "steering" current from one electrode to another to try to find a good therapeutic result for the patient. Current steering is discussed further in U.S. Pat. No. 7,890,182. As shown in FIG. 4A, the source current Iout=5 mA is shared between the selected electrodes E1 and E2, with the result that about half of this current would pass through each of switches S1 and S2, or about 2.5 mA. (The actual amount carried through the switches would depend on the resistive network R of the tissue between the selected electrodes). These currents rejoin at electrode E3, which sinks the entire 5 mA of current.

FIG. 4B shows an open circuit 63 in the path leading to E2. In this circumstance no current would flow through switch S2, and instead the entirety of the source current (5 mA) flows through switch S1 and electrode E1, and through electrode E3 and switch S3.

FIG. 4C shows a short circuit 64 in the path leading to electrode E1. In this circumstance, and assuming the short 64 is of low resistance, the entirety of the sourced current (5 mA) flows through switch S1 through the short 64, and no current (or negligible current) flows through S2 and electrode E2. As with FIG. 3C, effective grounding of electrode E3 prevents a significant current from flowing through electrode E3 and switch S3'.

The inventor finds the failures conditions of FIGS. 3B, 3C, 4B, and 4C regrettable, because in each case the selected electrodes are not receiving the amount of current desired, which ultimately affects patient therapy and potentially also impacts patient safety. A better solution for monitoring these and other failure conditions is therefore warranted, and is provided by this disclosure.

BRIEF DESCRIPTION OF THE DRAWINGS

FIGS. 1A and 1B show an implantable pulse generator (IPG), and the electrode arrays coupled to the IPG in accordance with the prior art.

FIGS. 2A and 2B show circuitry for distributing a therapeutic current between electrodes in the IPG of FIGS. 1A and 1B using switching matrices in accordance with the prior art.

FIGS. 5A, 5B, 6A, and 6B show embodiments of improved monitoring circuitry used to determine failure conditions in an IPG by monitoring the voltage drop across the switches used in the switching matrices.

FIGS. 10A-10C and 11A-11C show example measurements taken in accordance with the monitoring circuitry, and shows how the error check algorithm determines failure for different failure conditions.

DETAILED DESCRIPTION

Monitoring circuitry for an implantable stimulator device is disclosed. A switching matrix allows current from a current source to be distributed to any of a plurality of electrodes. A voltage drop across the active switches in the switch matrix is monitored and is compared to an expected voltage based upon the amplitude of the current and the known on resistance of the switch. If the monitored and expected voltages differ significantly, then a failure condition can be inferred, and an appropriate action can be taken, such as one or more of shutting down stimulation, setting of an alarm, logging the failure in memory, and telemetering the failure condition to a device external to the patient. Using the already-existing switches in the switching matrix in this fashion is beneficial because it allows the current through the electrodes to be monitored without providing additional structures in the therapeutic current path, which would increase complexity, add unwanted resistance, or possibly cause periodic or sporadic changes in therapeutic output.

Figure 5A:
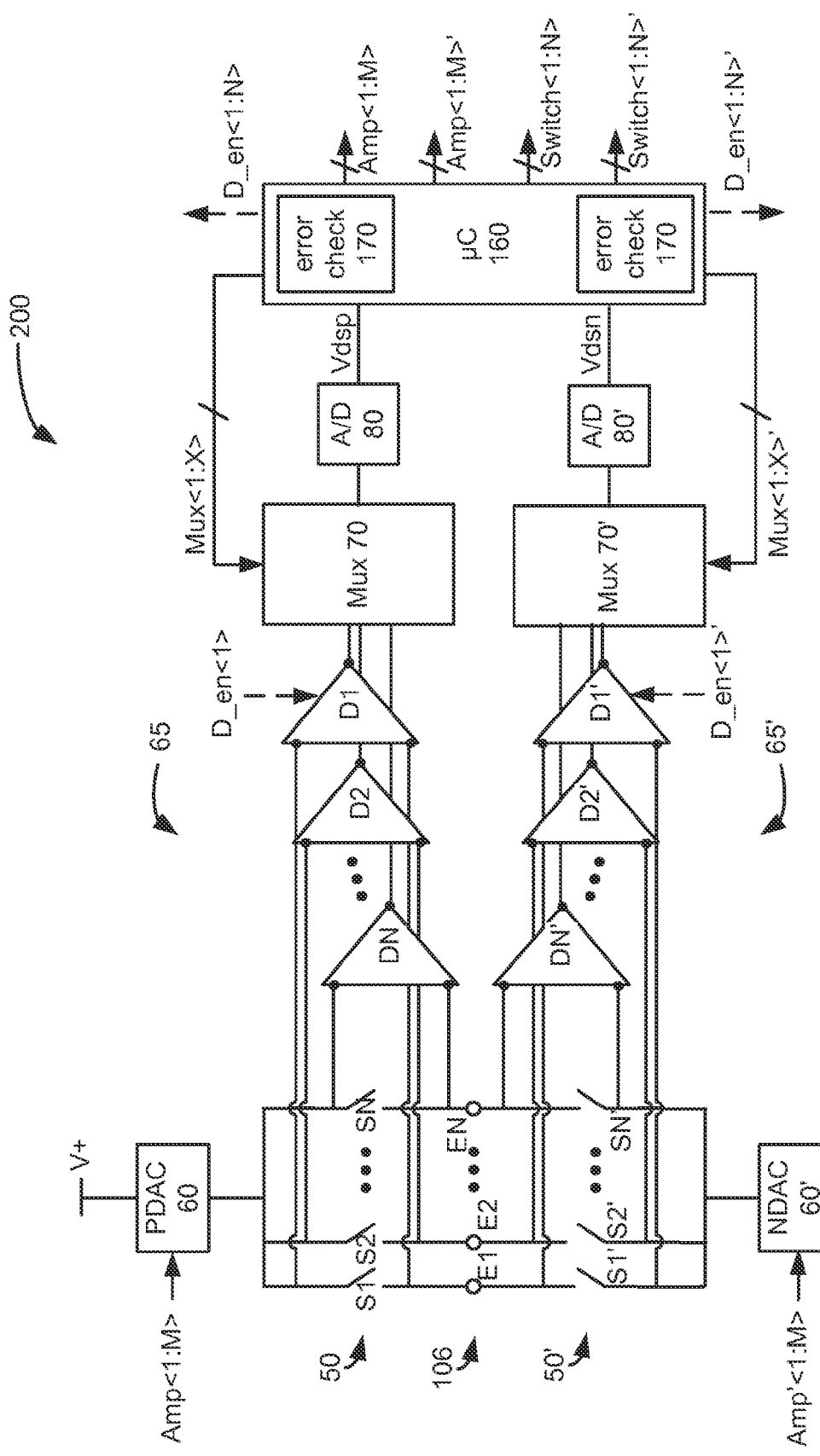

FIG. 5A illustrates a first example of improved monitoring circuitry 200 for an IPG, such as IPG 100 illustrated earlier. Shown are a number of differential amplifiers (diff amps) D1-DN 65 and D1'-DN' 65' each for measuring the voltage drop across one of the switches S1-SN and S1'-SN' in switching matrices 50 and 50'. The outputs of diff amps D1-DN 65 are coupled to a multiplexer 70, which can choose one of the outputs and pass it along to an Analog-to-Digital converter (A/D) 80. Similarly, the outputs of diff amps D1'-DN' 65' are coupled to a multiplexer 70', which can choose one of the outputs and pass it along to an Analog-to-Digital converter (A/D) 80'. The digitized outputs, Vdsp and Vdsn, are reported to the control circuitry 160, where they can be reviewed and appropriate action taken in conjunction with an error check algorithm 170, which will be explained in further detail later.

In one embodiment, improved monitoring circuitry 200 monitors the voltage across only those switches that are active (closed), and thus are involved in forming the current path through the tissue R. In this regard, the control circuitry 160, which knows which switches are implicated by virtue of switch control signals Switch<1:N> and Switch<1:N>', can issue appropriate mux control signals Mux<1:X> and Mux<1:X>' to the muxes 70 and 70'. This allows each mux to pass a Vdsn and Vdsp measurement to the A/D converters 80 and 80' and ultimately to the control circuitry 160.

Control circuitry 160 may issue enable signals, D_en<1:N> and D_en<1:N>' to enable only the diff amps 65 and 65' coupled to the active switches. This conserves power by only powering diff amps of interest, and further provides the ability to make Vdsp and Vdsn measurements at certain points in time, such as when pulses are actually being issued. Moreover, Vdsp and Vdsn may not be measured on active switches on every pulse, and thus D_en and D_en' may likewise not issue on every pulse; instead, these measurements may be taken every 100 pulses or so to occasionally verify correct operation of the IPG 100. The A/D converters 80 and 80' may also be selectively enabled, although controls signals for effecting this are not shown.

Figure 5B:
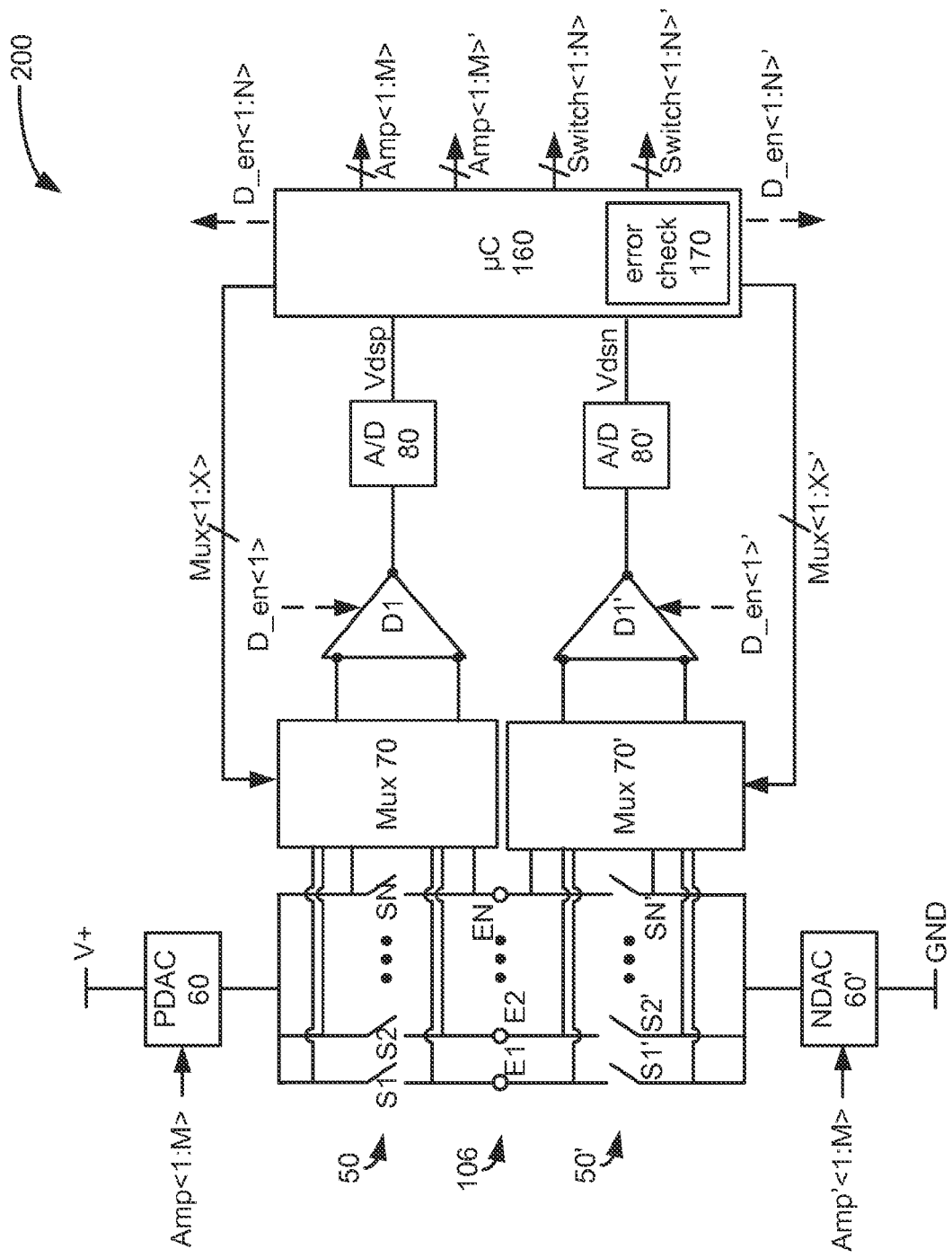

FIG. 5B shows a modification to the monitoring circuitry 200 in which the muxes 70 and 70' are positioned between the switches S1-SN and S1'-SN' and single diff amps D1 and D1'. In this modification, the muxes 70 and 70' pass signals from the selected switches through the muxes to the diff amps to measure the voltage drop. This modification is simpler as it reduces the number of diff amps, but may also suffer from losses in the measured signals as they pass through the muxes.

As noted earlier in conjunction with FIGS. 4A-4C, more than one electrode may be coupled to the PDAC 60 or the NDAC 60' at a time to share the sourced or sunk current. In this case, it may be desirable to monitor the voltage drop across more than one of the switches S1-SN or S1'-SN' at one time. FIG. 6A shows an example of alternative monitoring circuitry 200' useful for this purpose. As shown, each bank of diff amps sends their outputs to two muxes, with diff amps 65 sending their outputs to muxes 70a and 70b, and diff amps 65' sending their outputs to muxes 70a' and 70b'. This allows two Vdsp measurements (Vdspa and Vdspb) and two Vdsn measurements (Vdsna and Vdsnb) to be taken and digitized at one time. Increasing the number of muxes per each diff amp bank would allow for even further simultaneous measurements. As before, the diff amps 65 or 65' can be selectively enabled, although the enable control signals are not shown for simplicity. Although not shown, it should be understood that the mux control signals would be modified as necessary to handle the increased number of muxes.

FIG. 6B shows another embodiment for the monitoring circuitry 200" not using multiplexers. Here, each diff amp 65 or 65' is coupled to a dedicated A/D converter 80 or 80', producing, potentially simultaneously, N Vdsp measurements and N Vdsn measurements. This may be useful to monitor the voltage drops across all of the switches S1-SN and S1'-SN', even those that are closed, a subject discussed further below.

While the monitoring circuitry 200' and 200" of FIGS. 6A and 6B are particularly useful to simultaneously measure the voltage drop across switches that may share the sourced or sunk current, it should be noted that the monitoring circuitry 200 of FIGS. 5A or 5B could also be used, although it would not allow for such measurements to be taken simultaneously. For example, if both electrodes E1 and E2 are simultaneously selected to share the sourced current, as in FIG. 4A, mux 70 could for example select to monitor switch 51 (via D1) during a first pulse, and then select to monitor switch S2 (via D2) during a second pulse, etc. This might not allow detection of failure conditions immediately, but because pulses occur at a relatively high frequency (e.g., 50-200 Hz), any failures would be picked up in a short amount of time.

Figure 7:
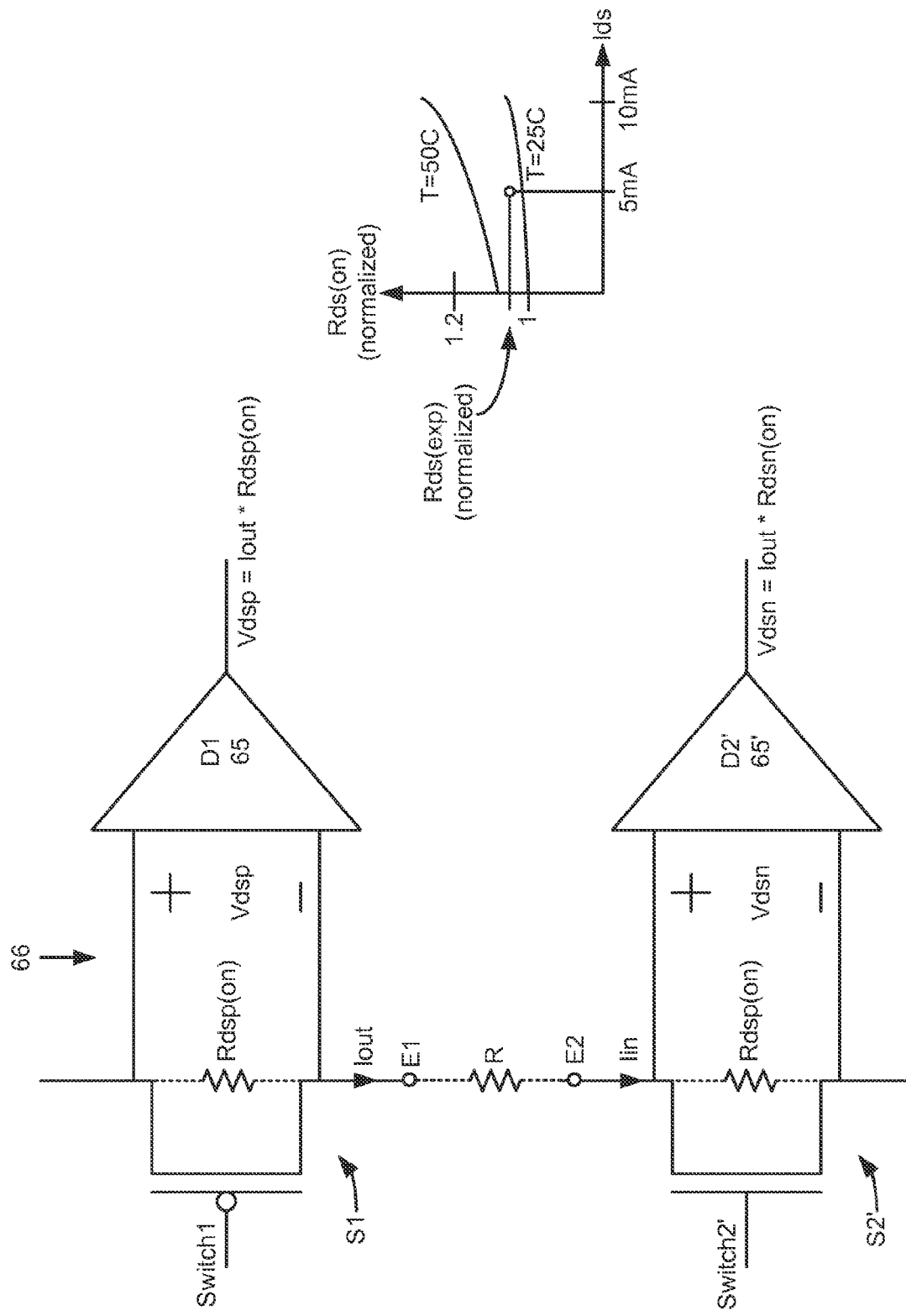
FIG. 7 shows further details of the measurement across the switches.

FIG. 7 shows further details of the therapeutic current path through selected electrodes E1 and E2, and their associated switches S1 and S2' and diff amps D1 and D2'. In FIG. 7 it is assumed, as is typical, that the switches S1 and S2' in the current path comprise MOSFET transistors. Each diff amp D1 and D2' receives as inputs taps 66 connected across each of the switches S1 and S2' respectively, such that one tap is connected to the drain of the switch, and the other to the source. If the switches comprise bipolar transistors, the taps would likewise connect to the emitter and collector of the switches. Configured in this fashion, each diff amp 65 is presented with and measures the drain-to-source voltage (Vds) across each switch, or more specifically Vdsp across the P-channel switches (such as S1) and Vdsn across the N-channel switches (such as S2'). (It is not required that the switches have these polarities in each of the switch matrices 50 and 50', although this is logical given the relative voltages that the switches experience. Note that P-channel switches S1-SN would be active low while the N-channel switches S1'-SN' would be active high. That is, switch control signal Switch1 would be a logic '0' to turn on switch S1, while Switch2' would be active high to turn on switch S2'). In accordance with Ohm's law, Vdsp and Vdsn will equal the product of the current through the switch (Iout=Iin) and the on resistance of the switches (Rdsp(on) and Rdsn(on)).

As illustrated in the graph to the right in FIG. 7, the on resistance Rds of the switches vary slightly with the amplitude of the current (Ids, or Iout=Iin) flowing through the switch, and also varies with temperature. Still, expected values or ranges for Rdsp and Rdsn, Rdsp(exp) and Rdsn(exp) can be known with fairly good certainty, particularly when typical ranges for Iout=Iin and temperature are known. The graph in FIG. 7 generically shows the determination of Rds (exp) assuming particular midrange values for the current (5 mA) and temperature (approximately 40C). Even if Rds(on) is not exactly known at any particular point in time, it will nonetheless be many orders of magnitude lower than the off resistance of the switches. In one example, Rdsp(exp) and Rdsn(exp) for the switches in switch matrices 50 and 50' are on the order of 10 Ohms. If necessary, the on resistances Rdsn(on) and Rdsp(on) can intentionally be set during design to provide a Vdsp and Vdsn that will be large enough to be resolved by the diff amps 65 and 65' and the A/D converters 80 and 80'. While intentionally raising Rds(on) is generally not desired from heat generation and power consumption perspectives, suitable values for Rds(on) to produce resolvable values for Vds will still be small and relatively insignificant.

Figure 8:
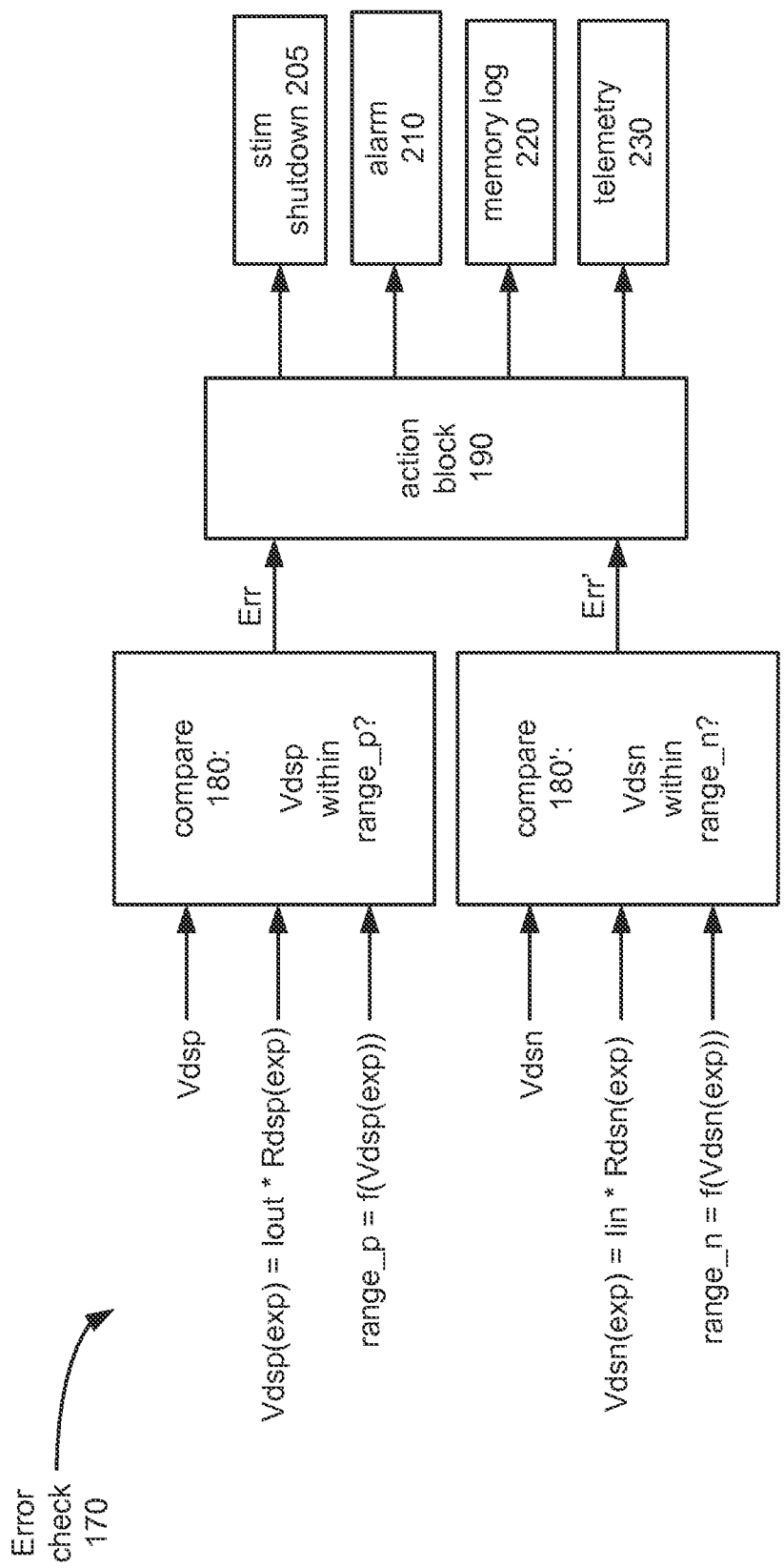
FIGS. 8, 9A, and 9B show embodiments of error check algorithms that are used to determine failure modes in accordance with the voltage drop measurements.

Error check algorithm 170 is depicted in FIG. 8 for the simple case of one Vdsp measurement (across a single one of the active switches S1-SN) and one Vdsn measurement (across a single one of the active switches S1'-SN'). As mentioned earlier, the error check algorithm 170 can be performed in the control circuitry 160, and may be implemented in firmware, or in any other well-known means such as software or hardware. As shown, error check algorithm 170 compares Vdsp and Vdsn as measured across the switches to expected values, i.e., Vdsp(exp) and Vdsn(exp), in blocks 180 and 180' respectively. Vdsp(exp) equals the current programmed to be sourced by PDAC 60, Iout, times the expected on resistance of the switch, Rdsp(exp), which is known and can be determined as discussed above. Similarly, Vdsn(exp) equals the current programmed to be sunk by NDAC 60', Iin (which should equal Iout), times the expected on resistance of the switch, Rdsn(exp), again as determined above.

Also, a comparative input is provided to each compare block 180 and 180' for some indication of a range (range_p; range_n) within which Vdsp and Vdsn measurements will be deemed acceptable, and not indicative of a failure condition in the IPG 100. Such ranges will comprise some function of the expected values Vdsp(exp) and Vdsn(exp), and can take several different forms. For example, it may only be of interest to know if the current through the switch is very low, or effectively zero. If so, Vdsp and Vdsn would necessarily be very small. To detect this condition, range_p for example might be set relative to a threshold, i.e., Vdsp>c*Vdsp(exp), where c is between 0 and 1. Using a scalar c to define the threshold is sensible given the variability in the system, particularly Rdsp (exp), which as noted earlier may not always perfectly reflect the on resistance of the switch. Thus, compare block 180 might assess for example whether Vdsp>0.7*Vdsp(exp), on the notion that values below this threshold could not be due to expected variability, but must instead be due to an unusually low current draw (Iout) through the switch, which would potentially indicate failure. Range_n could similarly be set to Vdsn>0.7*Vdsn(exp).

In another example, the ranges may also determine an upper limit for Vdsn and Vdsp. For example, range_p could comprise 0.7<Vdsp(exp)<1.3, and range_n could comprise 0.7<Vdsn(exp)<1.3. An upper limit is useful to detect different failure conditions, such as an excess of current through a switch.

If either of Vdsp or Vdsn are out of range, compare blocks 180 and 180' can issue error signals, Err and Err' to an action block 190. Action block 190 can take various actions depending whether one or both of the error signals are indicated. For example, the action block 190 can cause stimulation to shut down (205); issuance of an alarm condition (210), such as through an audible transducer in the IPG 100 if present; logging of the failure in memory in the IPG 100 (220) for later telemetry to a device external to the implant (220); or immediate telemetry of the failure condition to the external device (230), where a visual or audible alarm is triggered. Still other actions could be taken by action block 190, and these are merely some examples.

Figure 4C:
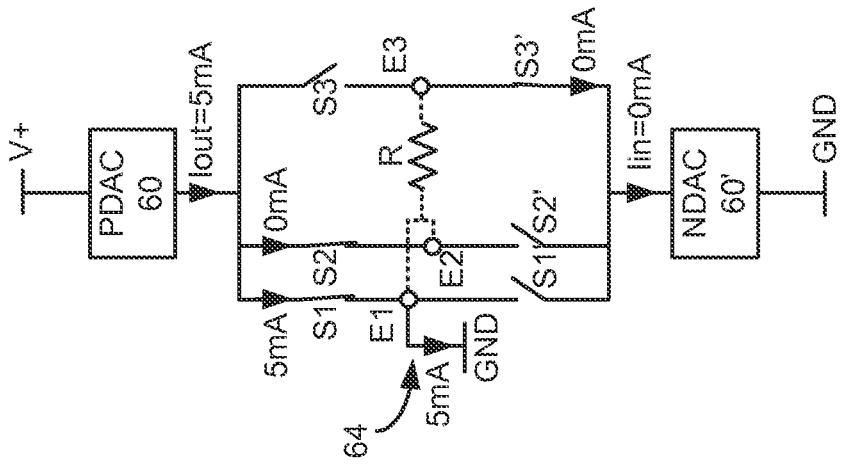
Figure 4B:
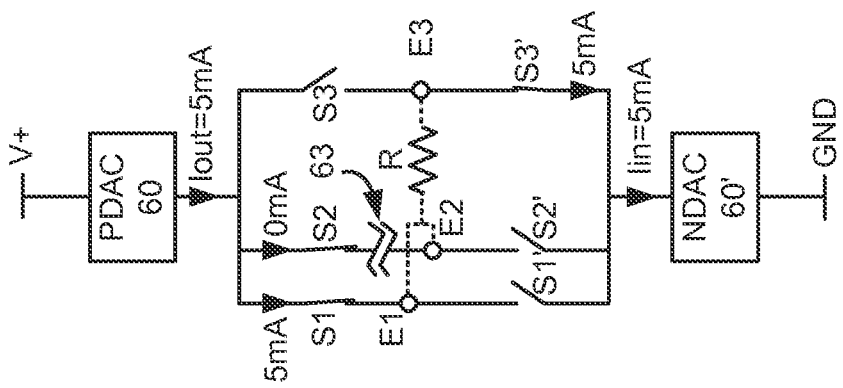
Figure 4A:
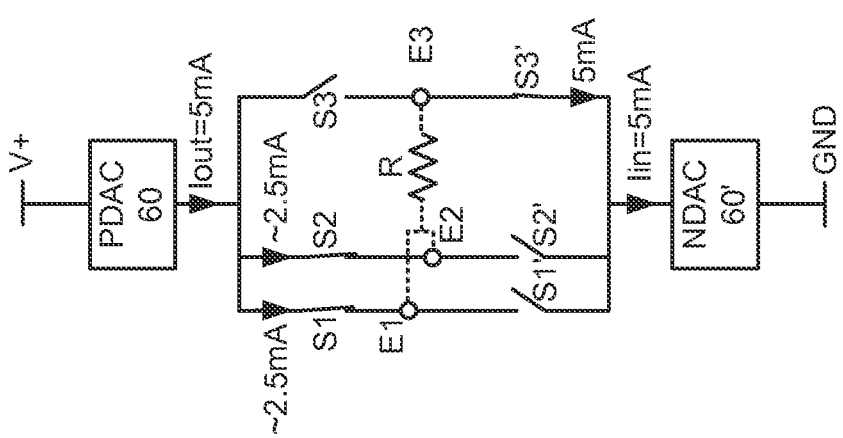
Figure 9A:
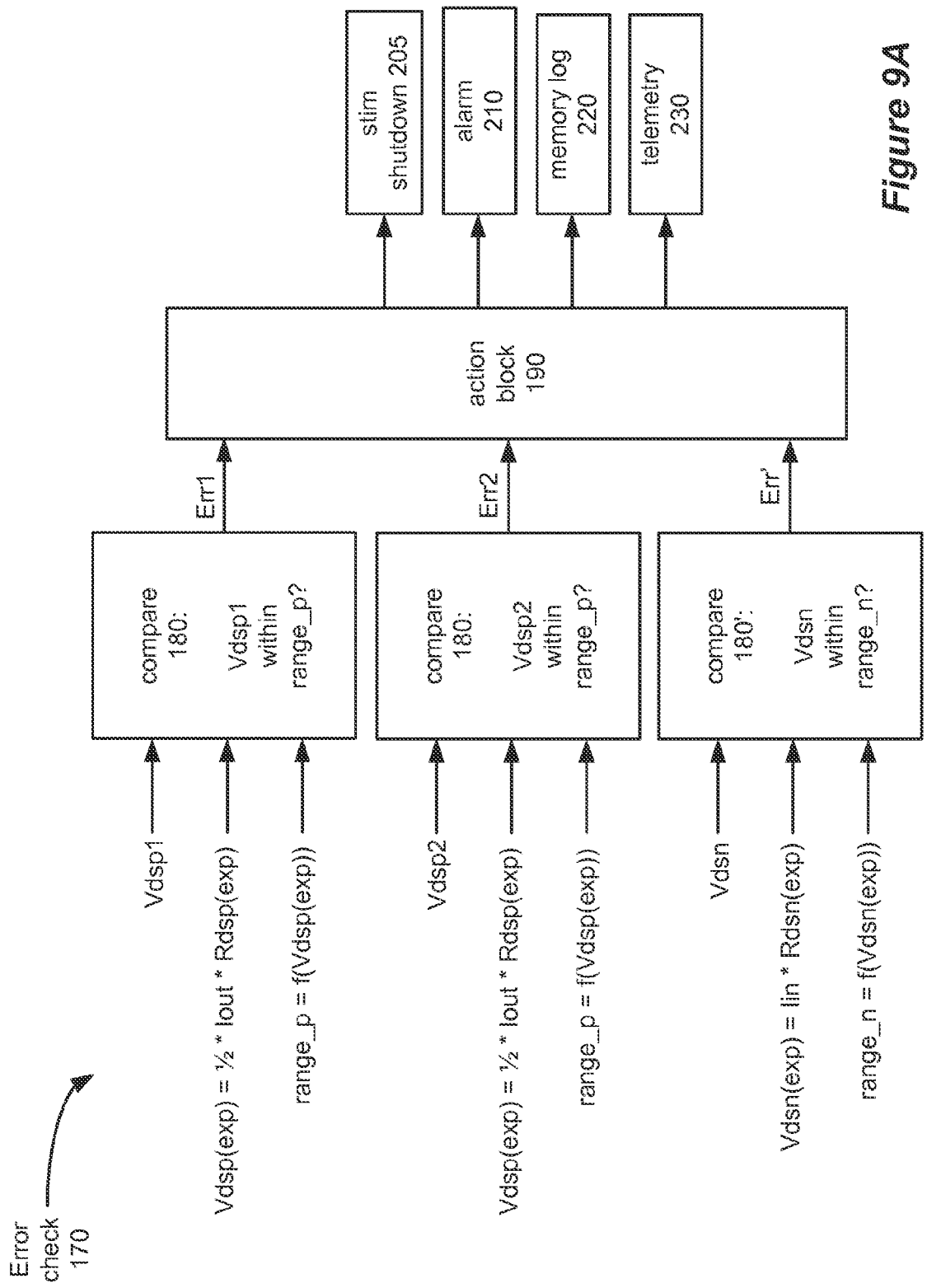

FIG. 9A illustrates a more-complicated example of the error check algorithm 170 when, as occurred in FIGS. 4A-4C, more than one electrode is coupled to the PDAC 60 and thus share the sourced current, Iout. (The error check algorithm 170 would similarly handle shared sunk current, Iin, between the switches in switch matrix 50' although this is not shown for convenience). In this circumstance, there are two Vdsp measurements (Vdsp1 and Vdsp2) taken across the active switches in switch matrix 50 (e.g., S1 and S2). It may not be known exactly what percentage of the shared current will be carried by each switch; this will depend on the resistive network R of the patient's tissue as well as the relative positions of the active electrodes. However, it is reasonable to approximate that each switch will carry one-half of the source current, i.e., ½ Iout. As a result, the expected voltage drop across the switches, Vdsp(exp), will each equal ½ Iout*Rdsp(exp).

Because this assumption of equal current splitting may not be accurate, the ranges used by the compare blocks 180 to determine suitable operation may be relaxed accordingly. For example, range_p may in this circumstance define a threshold of Vdsp>0.4*Vdsp(exp). The relaxed scalar (0.4) in this example appreciates not only that Rdsp(exp) may not accurately model the switch, but further that the amount of current drawn by the switch may be smaller than expected (i.e., smaller than ½Iout). As such, a wider range of tolerable values is used for range_p, but one which can still easily discriminate between conditions of low current and essentially no current.

Figure 9B:
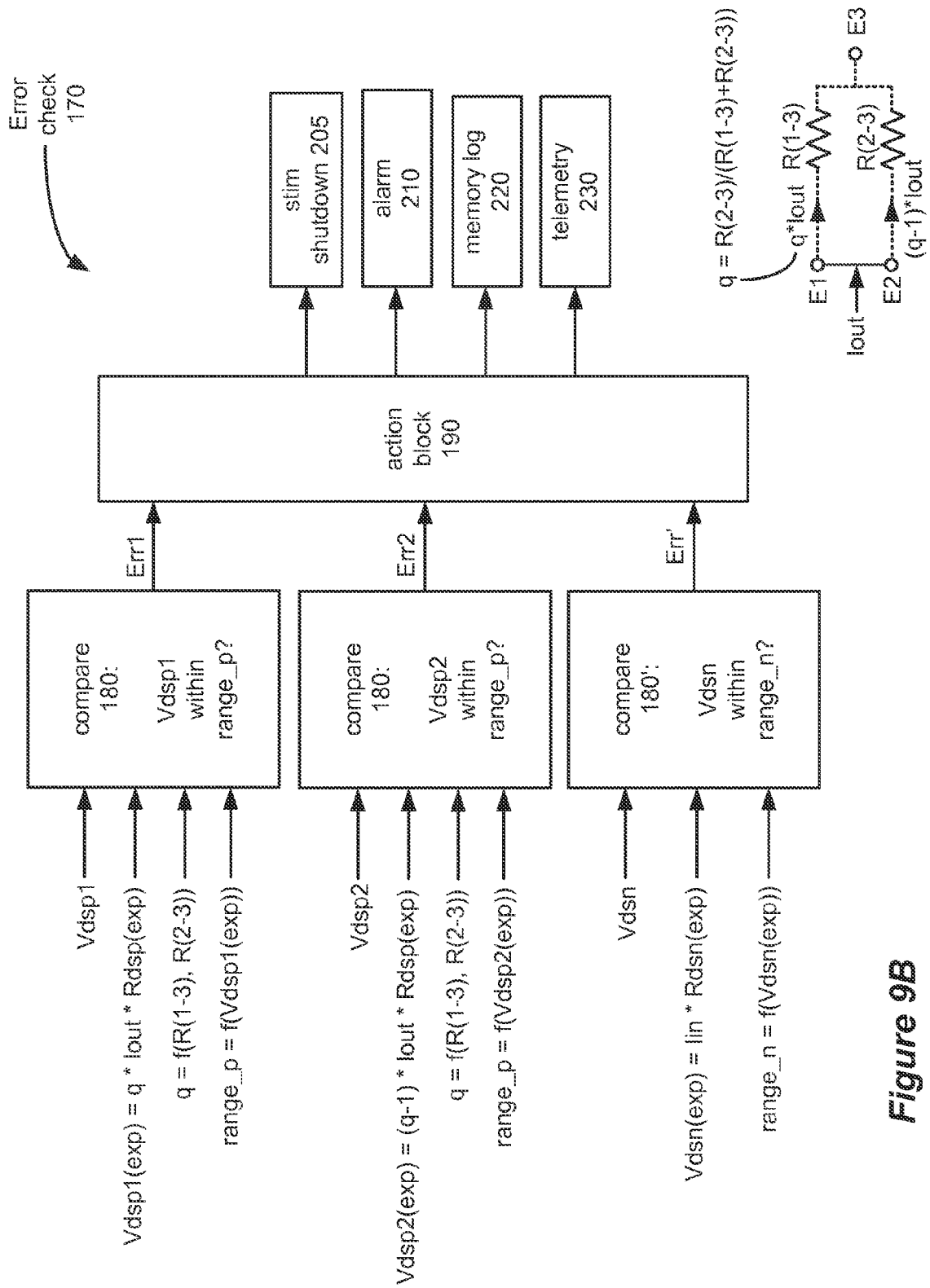

Alternatively, instead of assuming that each switch will equally share the sourced current, the resistance between the affected electrodes can be measured and used to deduce the ratio of Iout that each will carry, as illustrated in FIG. 9B. Measuring the resistance between electrodes in an IPG is well known, see e.g. U.S. Pat. No. 7,684,869, and thus circuitry and techniques for doing so are not discussed. Once the resistance between source electrode E1 and sink electrode E3 (R(1-3)) and between source electrode E2 and E3 (R(2-3)) have been measured, a ratio q (=R(2-3)/(R(1-3)+R(2-3))) can be calculated which describes what fraction of Iout will be carried through each of the source electrodes, i.e., E1 will carry q*Iout, and E2 will carry (q-1)*Iout, as shown in FIG. 9B at bottom right. Thus, q (or its constituents R(1-3) and R(2-3)) can be reported (e.g., from control circuitry 160) to each of the compare blocks 180, where it can then be used to estimate the expected voltage drops across S1 (Vdsp1(exp)) and S2 (Vdsp2(exp)). Due to the improved precision in estimating the expected current through the switches in FIG. 9B, the ranges used by the compare blocks 180 to determine suitable operation may not need to be as relaxed as they were in FIG. 9A. For example, range_p may in this circumstance define a threshold of Vdsp>0.7*Vdsp(exp), similar to what was used in FIG. 8 when expected currents through the switches were known.

Figure 3C:
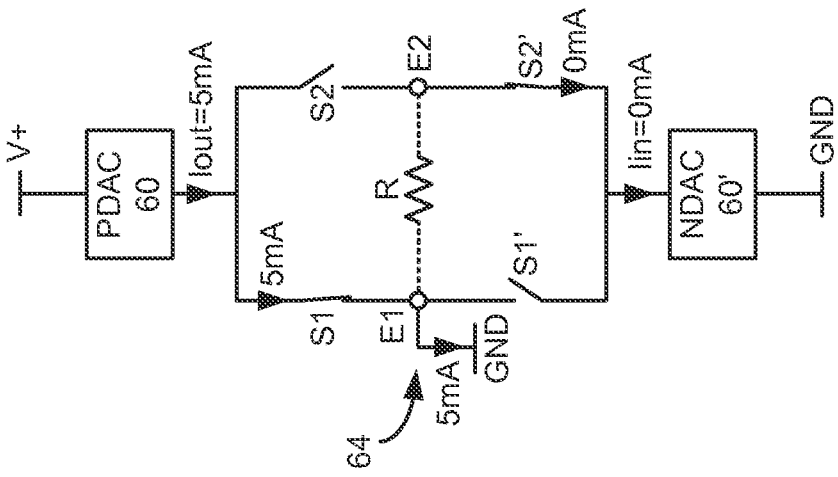
FIGS. 3A-3C and 4A-4C show different failure conditions that can arise in the current distribution circuitry of FIGS. 2A and 2B.
Figure 3B:
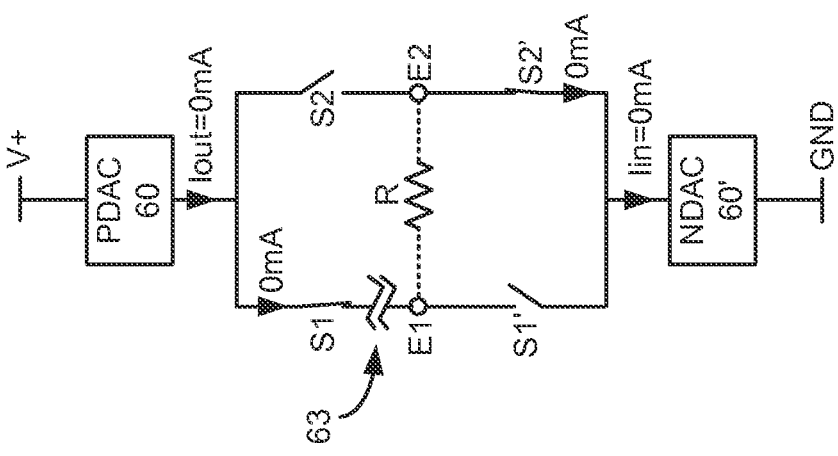
Figure 3A:
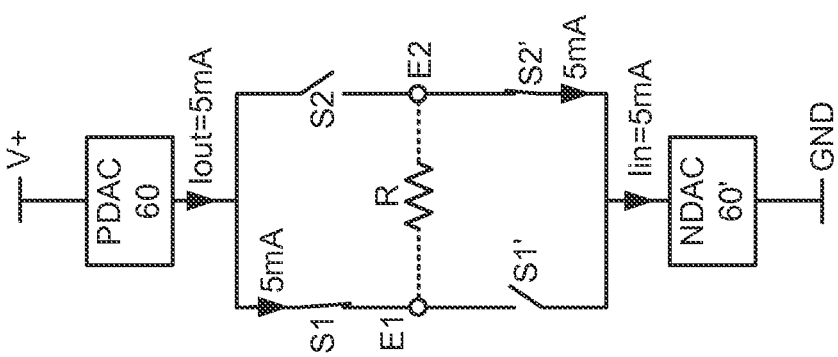

FIGS. 10A-10C revisit the conditions of FIGS. 3A-3C, in which current is passed from electrode E1 to E2, and shows the ability of the disclosed monitoring circuitry 200 to determine IPG failure. The values presented assume that both Rdsp(exp) and Rdsn(exp) equal 10 Ohms, and that both Vdsp(exp) and Vdsn(exp) will be deemed suitable if greater than 0.7* Iout=Iin * Rdsp(exp)=Rdsn(exp), or 0.35 mV. It is also assumed for simplicity that the actual on resistance of the switches equals the expected values of 10 Ohms.

In FIG. 10A both Vdsp1 and Vdsn2=50 mV, i.e., 5 mA * 10 Ohms. As these values are both above 35 mV, proper operation is inferred. FIGS. 10B and 10C respectively illustrate an open circuit 63 and a short circuit 64. In FIG. 10B, no current flows as discussed earlier (FIG. 3B). As a result, both Vdsp1 and Vdsn2 are essentially zero, and not greater than 35 mV. From this, the monitoring circuitry will assume that a failure has occurred, and will take appropriate action, in any of the ways discussed previously. In FIG. 10C, the short circuit 64 (assuming it is of significantly lower resistance than the tissue R as discussed earlier with respect to FIG. 3B) will pass all of the current through switch S1, and thus Vdsp=50 mV. By contrast, no current (or negligible current) will flow through switch S2', and thus Vdsn~0 mV. Thus, while Vdsp=50 mV infers proper operation, Vdsn does not, and thus the monitoring circuitry will assume that a failure has occurred, and again will take appropriate action, in any of the ways discussed previously.

FIGS. 11A-11C revisit the conditions of FIGS. 4A-4C, in which source current is shared by electrodes E1 to E2 and sunk by electrode E3, and shows the ability of the disclosed monitoring circuitry 200 to determine IPG failure. The values presented again assume that both Rdsp(exp) and Rdsn(exp) equal 10 Ohms. Vdsn(exp) will be deemed suitable if greater than 0.7*Iin*Rdsn, or 0.35 mV. As discussed in conjunction with FIG. 9A, Vdsp(exp) will be deemed suitable if greater than 0.4*½*Iout*Rdsp(exp), or 0.10 mV. It is again also assumed that the actual on resistance of the switches equals the expected values of 10 Ohms, and that the currents flowing through each of electrodes E1 and E2 are evenly split.

In FIG. 11A, both Vdsp1 and Vdsp2=25 mV, i.e., ½* 5 mA * 10 Ohms. As these values are both above the relaxed threshold of 10 mV, proper operation is inferred. Vdsn3=50 mV, i.e., 5 mA * 10 Ohms, which is above 35 mV, and which also infers proper operation. In FIGS. 11B and 11C, respectively illustrating an open circuit 63 and a short circuit 64, the currents are unbalanced, with all of the sourced current flowing through switch S1, and none through S2. As a result, Vdsp1, like Vdsn3, equals 50 mV, which is above 10 mV and infers proper operation. (Note however that if $range_{13}$ p defines an upper threshold for Vdsp1, 50 mV might exceed this upper threshold, and thus be deemed a failure condition). Vdsp2 by contrast is essentially zero, which does not exceed even the relaxed threshold of 10 mV. As a result, the monitoring circuitry will assume that a failure occurred, and will take appropriate action in any of the ways discussed previously.

Figure 12C:
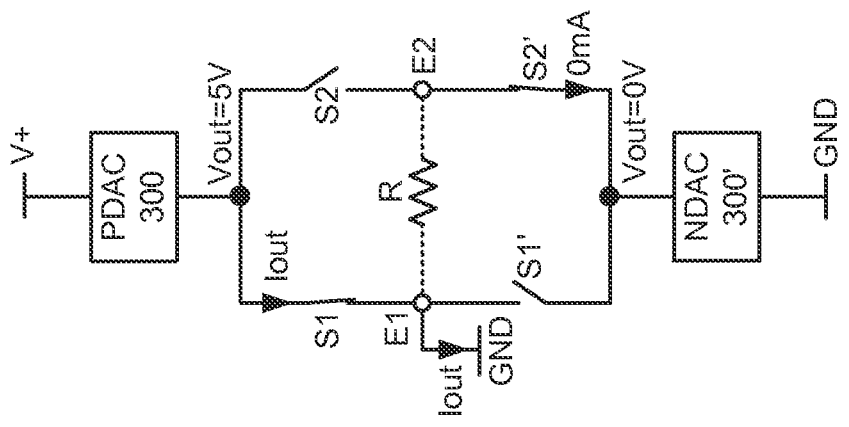
FIGS. 12-15 show variations of the current distribution circuitry useable with the monitoring circuitry and error check algorithm.
Figure 12B:
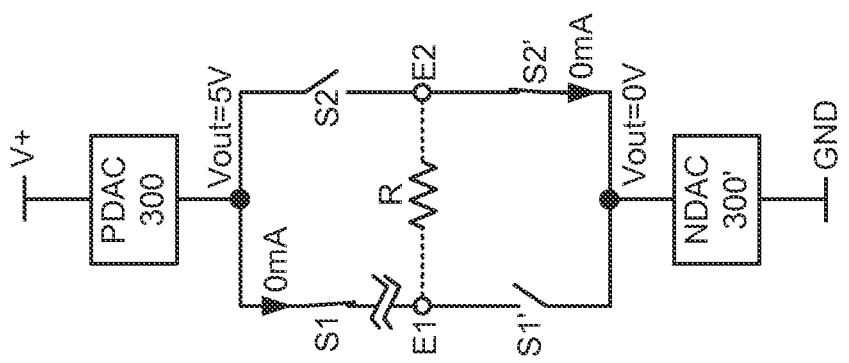
Figure 12A:
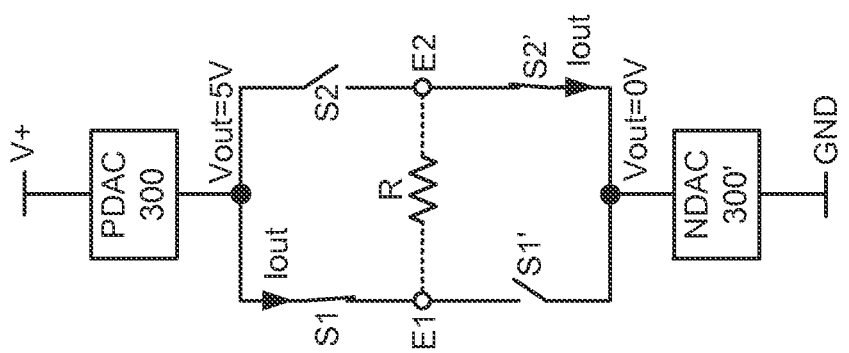

To this point, it has been assumed that therapeutic current is driven through the patient's tissue using constant current sources and sinks, such as PDAC 60 and NDAC 60'. However, use of the disclosed monitoring circuitry 200 is not limited to the use of such sources, and constant voltage sources could also be used. In FIGS. 12A-12C, constant voltage sources 300 and 300' are used to set known voltages at their outputs, such as Vout1=5 V and Vout2=0 V as shown. When constant voltages are used, the current through the switches must be estimated based on the resistances present, including the on resistance of the switches (Rds(exp)) and the resistance of the patient's tissue R. R can be estimated based on past experience, or can be measured as discussed above in conjunction with FIG. 9B. The series resistance of both switches Rdsp (exp) and Rdsn(exp) and the tissue R establish a voltage divider, and the expected voltage drop across each switch would equal Vdsp(exp)=(Vout1-Vout2)*(Rdsp(exp)/(Rdsp(exp)+Rdsn(exp)+R)) and Vdsn(exp)=(Vout1-Vout2)*(Rdsp(exp)/(Rdsp(exp)+Rdsn(exp)+R)).

Thus, values for Vdsp(exp) and Vdsn(exp) can generally be determined as a function of the potential difference between the two constant voltage courses 300 and 300'. Such values, perhaps as relaxed by range_p and range_n as discussed earlier, can thus be used to differentiate relative levels of current through the switches, and thus can be used by the error check algorithm 170 to determine failure conditions. A "current source" as used herein should be understood as comprising both constant current sources or sinks, constant voltage sources or sinks, or non-constant versions thereof.

Figure 13C:
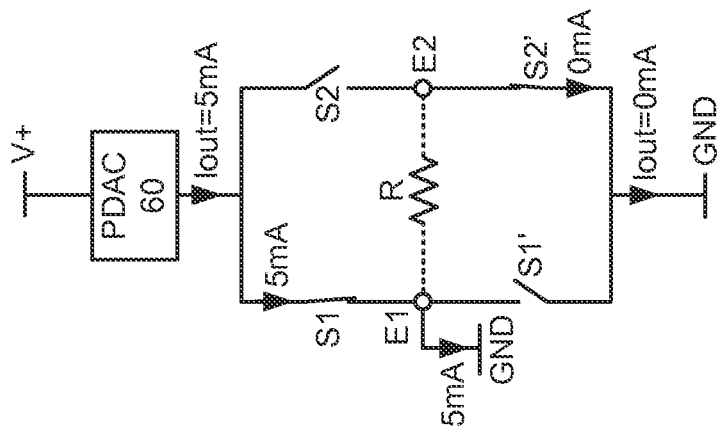
Figure 13B:
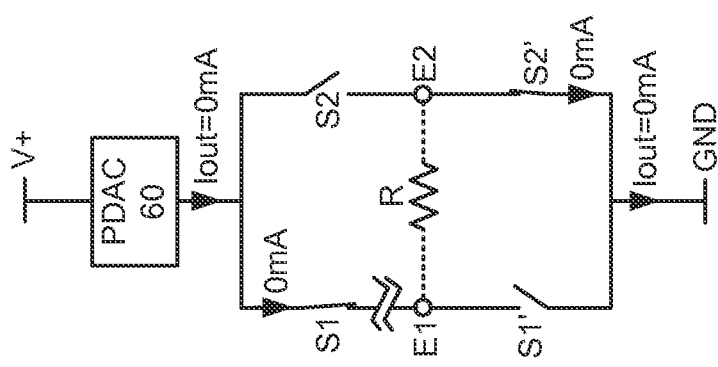
Figure 13A:
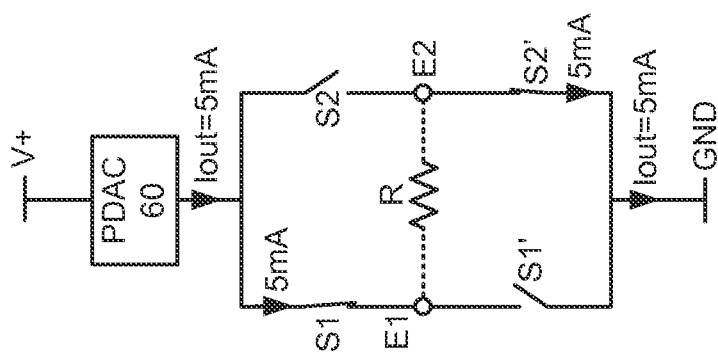

It is also not necessary that two current or voltages sources be used. For example, FIGS. 13A-13C show examples in which only a constant current PDAC 60 is used to source a current; there is no corresponding active sink, and instead the sourced current travels passively to ground as a reference potential. Although not shown, the single source could also comprise a constant voltage source, such as PDAC 300 discussed with reference to FIGS. 12A-12C. Further, and again although not shown, the single source could be on the return side of the current. Thus, for example, there could be a single NDAC 60 used to actively sink a current, with the compliance voltage V+ acting as a passive reference potential to source the current. Thus, regardless of the particular configuration of the current distribution circuitry, error check algorithm 170 can still be used to monitor the voltage drops across the switches and to determine whether failures conditions exist.

Figure 14:
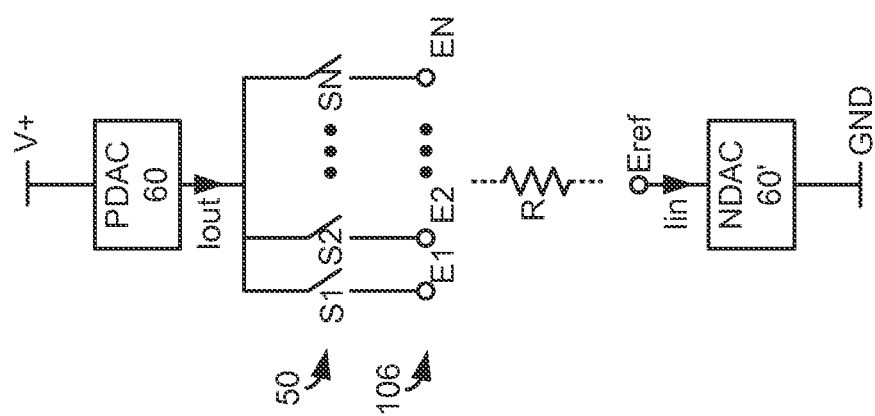

Similarly, the error check algorithm 170 is also useable with a single switch matrix 50, as shown in FIG. 14. In this example, there is no corresponding switch matrix 50' (compare FIG. 2A), and instead sourced current flows through a selected electrode (or electrodes), through the tissue R, and back to the device through a reference electrode, Eref. Eref could comprise for example the conductive case 30 of the IPG 100 (FIG. 1A). As with earlier embodiments, error check algorithm 170 can still be used to monitor the voltage drops across the switches and to determine whether failures conditions exist.

Even if two switching matrices 50 and 50' are used, it is not necessary to measure active switches in both of these matrices, although this is preferred to get a complete picture of where failure may be occurring in the IPG 100. It is further not necessary to measure active switches in both matrices 50 and 50' at the same time. For example, the switches in switch matrix 50 could be measured during the issuance of even pulses, and the switches in switch matrix 50' could be measured during the issuance of odd pulses. If this type of modification is used, one could modify the monitoring circuitry 200 of FIGS. 5A or 5B to use a single multiplexer 70 and A/D converter 80.

Figure 15:
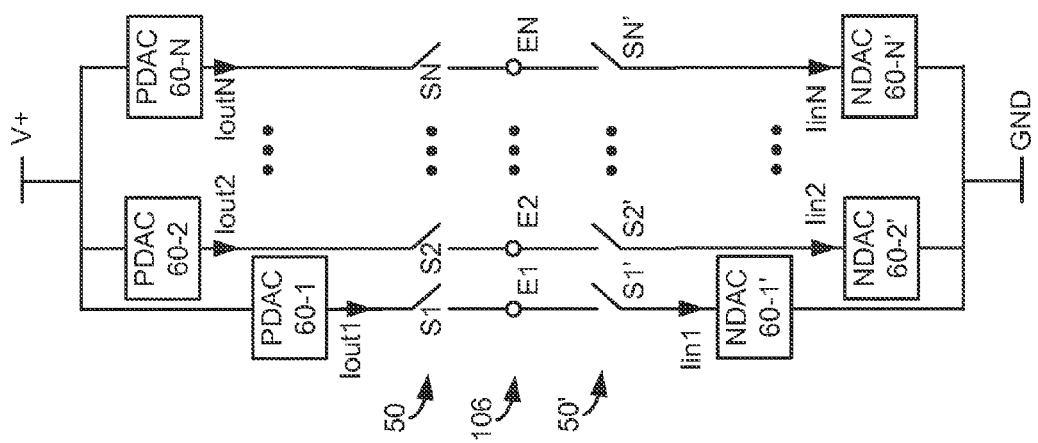

It is not necessary when using disclosed monitoring circuitry that the current sources be shared between the electrodes. For example, as shown in FIG. 15, each electrode (Ex) is provided a dedicated constant current source (PDAC 60-x) and constant current sink (NDAC 60-x'), each programmable to produce currents of adjustable amplitudes (Ioutx and Iinx; amplitude adjustment signals not shown). Once again, monitoring circuitry and error check algorithms such as those disclosed can be used to monitor the voltage drops across the switches and to determine whether failures conditions exist. Note that when the architecture of FIG. 15 is used, determining Vdsp(exp) and Vdsn(exp) is easier because the expected currents through the switches are determined by their associated current sources or sinks (e.g., Vdsp1(exp)=Iout1*Rdsp (exp)). Because sourced or sunk currents are not shared from a common PDAC 60 or NDAC 60', relative expected amounts of currents carried by each switch need not be estimated or measured.

Although to this point it has been assumed that the monitoring circuitry measures the voltage only across active switches to deduce failure conditions, this is not strictly necessary. For example, monitoring circuitry 200" of FIG. 6B can measure the voltage drops across all of the switches, regardless of whether they are currently on, to route the therapeutic current. Monitoring non-active (off) switches can be useful to deduce other sorts of failure conditions. For example, because no current should flow through a switch that is off, the voltage drop across that switch should be zero (or negligible). If a significant voltage drop is nonetheless detected, this would indicate that the switch is leaking, and is carrying at least some amount of the therapeutic current when it should not. As with the other failure conditions discussed herein, action block 190 can assess this result and take appropriate action.

A benefit of the disclosed monitoring circuitry is that it allows proper IPG function to be determined in situ during the issuance of actual therapeutic currents (pulses). However, it is not so limited. Instead, or in addition, the monitoring circuitry can be used during periods when the IPG is not active, such as before beginning actual therapeutic stimulation. In this manner, each of the electrodes can be tested with a relatively low amplitude test current not intended as therapy for the patient and perhaps not likely to be noticed by the patient, such as Iout=Iin=0.5 mA. Each of the electrodes can be cycled through, the voltage drop across its associated switch monitored, and an assessment of failure made before commencing actual stimulation. Only the electrodes to be used during actual stimulation may be tested in this manner, or all electrodes may be tested even if they are not immediately to be used. Additionally, test pulses of this type can be interleaved with actual stimulation pulses. Thus, actual stimulation pulses can be issued at frequency f, with lower-amplitude test pulses issued at the same frequency, but 180-degrees out of phase with the actual stimulation pulses.

One skilled in the art will understand that any modification disclosed herein can be used in combination with the other disclosed modifications.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable stimulator device, comprising:
    a plurality of electrodes;
    at least one current source configured to produce at least one current;
    a plurality of switches, wherein the switches are selectable to distribute the at least one current to or from one or more of the electrodes; and
    monitoring circuitry configured to measure at least one voltage, each at least one voltage comprising a voltage only across one of the switches, and for determining whether a failure condition has occurred.

2. The implantable stimulator device of claim 1, wherein the monitoring circuitry determines whether a failure condition has occurred by comparing the at least one voltage to an expected range.

3. The implantable stimulator device of claim 2, wherein the expected range is based on an on resistance of the switch.

4. The implantable stimulator device of claim 2, wherein the expected range is defined by a single threshold.

5. The implantable stimulator device of claim 2, wherein the expected range is defined by a lower threshold and an upper threshold.

6. The implantable stimulator device of claim 1, wherein there are N switches corresponding to N electrodes.

7. The implantable stimulator device of claim 1, wherein the at least one current source comprises at least one constant current source, and wherein the at least one current comprises at least one constant current.

8. The implantable stimulator device of claim 7, wherein an amplitude of the at least one constant current is adjustable at the at least one constant current source.

9. The implantable stimulator of claim 7, wherein the at least one constant current source either sources at least one current to the one or more electrodes, or sinks at least one current from the one or more electrodes.

10. The implantable stimulator device of claim 1, wherein the at least one current source comprises at least one constant voltage source for producing at least one constant voltage to produce the at least one current.

11. The implantable stimulator device of claim 10, wherein an amplitude of the at least one constant voltage is adjustable at the at least one constant voltage source.

12. The implantable stimulator device of claim 1, wherein the monitoring circuitry is configured to only measure the at least one voltage only across the switches that are selected to distribute the at least one current to or from the one or more of the electrodes.

13. The implantable stimulator device of claim 1, wherein the monitoring circuitry is configured to measure the at least one voltage only across switches that not are selected to distribute the at least one current to or from the one or more of the electrodes.

14. The implantable stimulator device of claim 1, wherein the monitoring circuitry is configured to measure the at least one voltage only across all of the switches.

15. The implantable stimulator device of claim 1, wherein the at least one current comprises a therapeutic current for stimulating a patient's tissue, and wherein the monitoring circuitry is configured to measure the at least one voltage during the provision of the therapeutic current to the patient's tissue.

16. The implantable stimulator device of claim 1, wherein the at least one current comprises a test current not intended as therapy for a patient, and wherein the monitoring circuitry is configured to measure the at least one voltage during the provision of the test current.

17. The implantable stimulator device of claim 1, wherein the monitoring circuitry comprises at least one voltage amplifier for measuring the at least one.

18. The implantable stimulator device of claim 1, wherein the failure condition comprises an open circuit or a short circuit of one of the electrodes.

19. The implantable stimulator device of claim 1, wherein the monitoring circuitry further comprises control circuitry, wherein the failure condition is reported to the control circuitry to enable an action.

20. The implantable stimulator device of claim 19, wherein the action comprises one or more of stopping the current, issuing an alarm, logging the failure condition in a memory in the implantable stimulator device, or telemetry of the failure condition to a device external to the implantable stimulator device.

21. The implantable stimulator device of claim 1, wherein first and second of the switches are selected to distribute the at least one current to two electrodes, and wherein the monitoring circuitry is configured to measure a first voltage only across the first switch and a second voltage only across the second switch to determine whether a failure condition has occurred.

22. The implantable stimulator device of claim 21, wherein the first and second voltages are measured simultaneously.

23. The implantable stimulator device of claim 21, wherein the first and second voltages are not measured simultaneously.

24. The implantable stimulator device of claim 1, wherein there is only one current source configured to produce one current.

25. An implantable stimulator device, comprising:
    a plurality of electrodes;
    at least one current source configured to produce at least one current;
    a plurality of switches, wherein the switches are selectable to distribute the at least one current to or from one or more of the electrodes; and
    monitoring circuitry configured to measure a voltage across each selected switch individually and for determining whether a failure condition has occurred.

26. The implantable stimulator device of claim 25, wherein the monitoring circuitry determines whether a failure condition has occurred by comparing the voltage across each selected switch to an expected range.

27. The implantable stimulator device of claim 26, wherein the expected range is based on an on resistance of the switch.

28. The implantable stimulator device of claim 26, wherein the expected range is defined by a single threshold.

29. The implantable stimulator device of claim 26, wherein the expected range is defined by a lower threshold and an upper threshold.

30. The implantable stimulator device of claim 25, wherein the at least one current source comprises at least one constant current source, and wherein the at least one current comprises at least one constant current.

31. The implantable stimulator device of claim 30, wherein an amplitude of the at least one constant current is adjustable at the at least one constant current source.

32. The implantable stimulator of claim 30, wherein the at least one constant current source either sources at least one current to the one or more electrodes, or sinks at least one current from the one or more electrodes.

33. The implantable stimulator device of claim 25, wherein the at least one current source comprises at least one constant voltage source for producing at least one constant voltage to produce the at least one current.

34. The implantable stimulator device of claim 33, wherein an amplitude of the at least one constant voltage is adjustable at the at least one constant voltage source.

35. The implantable stimulator device of claim 25, wherein the monitoring circuitry is further configured to measure a voltage across switches that not are selected to distribute the at least one current to or from the one or more of the electrodes.

36. The implantable stimulator device of claim 25, wherein the at least one current comprises a therapeutic current for stimulating a patient's tissue, and wherein the monitoring circuitry is configured to measure the voltage across each selected switch during the provision of the therapeutic current to the patient's tissue.

37. The implantable stimulator device of claim 25, wherein the at least one current comprises a test current not intended as therapy for a patient, and wherein the monitoring circuitry is configured to measure the voltage across each selected switch during the provision of the test current.

38. The implantable stimulator device of claim 25, wherein the monitoring circuitry comprises at least one amplifier for measuring the voltage across each selected switch.

39. The implantable stimulator device of claim 25, wherein the failure condition comprises an open circuit or a short circuit of one of the electrodes.

40. The implantable stimulator device of claim 25, wherein the monitoring circuitry further comprises control circuitry, wherein the failure condition is reported to the control circuitry to enable an action.

41. The implantable stimulator device of claim 25, wherein the voltages across each selected switch are measured simultaneously.

42. The implantable stimulator device of claim 25, wherein the voltages across each selected switch are not measured simultaneously.

* * * * *